United States Patent [19]

Reif et al.

[11] Patent Number: 5,530,127
[45] Date of Patent: Jun. 25, 1996

[54] PREPARATION OF AMINES

[75] Inventors: Wolfgang Reif, Frankenthal; Lothar Franz, Mutterstadt; Peter Stops, Altrip; Volkmar Menger, Neustadt; Rainer Becker, Bad Dürkheim; Rudolf Kummer, Frankenthal; Siegfried Winderl, Heidelberg, all of Germany

[73] Assignee: BASF Aktiengesellschaft, Ludwigshafen, Germany

[21] Appl. No.: 509,997

[22] Filed: Aug. 1, 1995

[30] Foreign Application Priority Data

Aug. 8, 1994 [DE] Germany ............... 44 28 004.1

[51] Int. Cl.⁶ .................. C07C 209/16; C07D 295/023
[52] U.S. Cl. ................. 544/106; 564/347; 564/349; 564/480
[58] Field of Search ............... 544/106; 564/480, 564/349, 347

[56] References Cited

U.S. PATENT DOCUMENTS 4,014,933  3/1977  Boettger et al. .
4,151,204  4/1979  Ichikawa et al. .
5,002,922  3/1991  Irgang et al. .
5,166,433  11/1992  Irgang et al. ............ 564/480

FOREIGN PATENT DOCUMENTS 0254335  1/1988  European Pat. Off. .

Primary Examiner—Robert W. Ramsuer
Attorney, Agent, or Firm—John H. Shurtleff

[57] ABSTRACT

A process for the preparatiion of an amine which comprises reacting a primary or secondary alcohol and a nitrogen compound selected from the group consisting of ammonia and primary and secondary amines, at temperatures of from 80° to 250° C. and pressures of from 1 to 400 bar using hydrogen in the presence of a zirconium/copper/nickel catalyst, wherein the catalytically active material contains from 20 to 85 wt % of oxygen-containing zirconium compounds, calculated as $ZrO_2$, from 1 to 30 wt % of oxygen-containing compounds of copper, calculated as CuO, from 30 to 70 wt % of oxygen-containing compounds of nickel, calculated as NiO, from 0.1 to 5 wt % of oxygen-containing compounds of molybdenum, calculated as $MoO_3$ and from 0 to 10 wt % of oxygen-containing compounds of aluminum and/or manganese, calculated as $Al_2O_3$ or $MnO_2$, respectively.

10 Claims, No Drawings

PREPARATION OF AMINES

The present invention relates to a process for the catalytic amination of alcohols with nitrogen compounds and hydrogen in the presence of a zirconium/copper/nickel catalyst at elevated temperatures and pressures using zirconium/copper/nickel catalysts whose active material contains oxygen-containing compounds of molybdenum.

DE-A 1,953,263 discloses that it is possible to prepare amines by hydrogenative amination of the corresponding alcohols over catalysts containing cobalt, nickel and copper. The support material used in these catalysts is aluminum or silicon dioxide. With these catalysts good yields can be obtained at high temperatures and pressures. If the process is carried out at lower temperatures and pressures, the conversion and selectivity drop steeply.

EP-A 254,335 discloses Ni/Co/Ru catalysts on aluminum oxide or silicon dioxide supports, which additionally contain halides in their active material, for the hydrogenative amination of alcohols. Using these catalysts, conversions of only 61% maximum are achieved at 200° C. and 55 bar.

U.S. Pat. No. 4,151,204 discloses catalysts for the preparation of amino alcohols, which consist of a metal such as cobalt, nickel or copper, preferably nickel or cobalt, and which are optionally doped with small amounts of zirconium, the zirconium being added, in relation to the nickel or cobalt, in a molar ratio of from 0.005:1 to 0.2:1. Higher zirconium contents lead to side reactions such as decomposition of the products.

EP-A 382,049 discloses catalysts and processes for the hydrogenative amination of alcohols. These catalysts, whose active material contains oxygen-containing zirconium, copper, cobalt, and nickel compounds, are characterized by good activity and selectivity, but they have unsatisfactory maximum on-stream times.

It was thus the object of the present invention to overcome the aforementioned drawbacks.

Accordingly, we have found a novel and improved process for the preparation of amines from primary or secondary alcohols and nitrogen compounds selected from the group consisting of ammonia and primary and secondary amines, at temperatures of from 80° to 250° C. and pressures of from 1 to 400 bar using hydrogen in the presence of a zirconium/copper/nickel catalyst, wherein the catalytically active material contains from 20 to 85 wt % of oxygen-containing zirconium compounds, calculated as $ZrO_2$, from 1 to 30 wt % of oxygen-containing compounds of copper, calculated as $CuO$, from 30 to 70 wt % of oxygen-containing compounds of nickel, calculated as $NiO$, from 0.1 to 5 wt % of oxygen-containing compounds of molybdenum, calculated as $MoO_3$, and from 0 to 10 wt % of oxygen-containing compounds of aluminum and/or manganese, calculated as $Al_2O_3$ or $MnO_2$ respectively.

It is preferred to prepare amines of the general formula I

in which $R^1$ and $R^2$ denote hydrogen, $C_1$–$C_{20}$alkyl, $C_3$–$C_{12}$ cycloalkyl, aryl, $C_7$–$C_{20}$ aralkyl and $C_7C_{20}$ alkylaryl or together form $(CH_2)_l$—X—$(CH_2)_m$, $R^3$ and $R^4$ denote hydrogen, $C_1$–$C_{200}$ alkyl, $C_3$–$C_{12}$ cycloalkyl, $C_1$–$C_{20}$ hydroxyalkyl, $C_1$–$C_{20}$ alkyl substituted by amino and/or hydroxy, $C_2$–$C_{30}$ alkoxyalkyl, $R^5$—$(OCR^6R^7CR^8R^9)_n$—$(OCR^6R^7)$, aryl, $C_7$–$C_{20}$ aralkyl, $C_7$–$C_{20}$ alkylaryl, $(R^5)_2N$—$(CH_2)_q$ and Y—$(CH_2)_m$—$NR^5$—$(CH_2)_q$ or together form $(CH_2)_l$—X—$(CH_2)_m$ or $R^2$ and $R^4$ together form $(CH_2)_l$—X—$(CH_2)_m$, $R^5$ denotes hydrogen, $C_1$–$C_4$ alkyl, or $C_{12}$–$C_{40}$ alkylphenyl, $R^6$, $R^7$, $R^8$, and $R^9$ denote hydrogen, methyl, or ethyl, $R^{10}$ denotes hydrogen or $C_1$—$C_4$ alkyl, X denotes $CH_2$, oxygen, or N—$R^6$, Y denotes $N(R^5)_2$, hydroxy, $C_2$–$C_{20}$ alkylaminoalkyl or $C_3$–$C_{20}$dialkylaminoalkyl, n is an integer from 1 to 30, l is an integer from 2 to 4, m and q are integers from 1 to 4, from primary or secondary alcohols of the general formula II

and nitrogen compounds of the general formula III

in which $R^1$, $R^2$ and $R^3$ and $R^4$ have the aforementioned meanings.

Suitable alcohols are virtually all of the primary and secondary aliphatic alcohols. The aliphatic alcohols can be straight-chained, branch-chained, or cyclic. Secondary alcohols are equally well aminated as primary alcohols. No limitations are as yet known as regards the carbon number of aminatable alcohols. Furthermore the alcohols can carry substituents which are inert under the conditions of the hydrogenative amination, for example, alkoxy or alkyleneoxy groups. If polybasic alcohols are to be aminated, it is possible, via control of the reaction conditions, to obtain amino alcohols, cyclic amines, or polyaminated products.

The following alcohols are preferably aminated, for example:

Methanol, ethanol, n-propanol, isopropanol, n-butanol, isobutanol, n-pentanol, n-hexanol, 2-ethylhexanol, tridecanol, stearyl alcohol, palmityl alcohol, cyclopentanol, cyclohexanol, ethanolamine, n-propanolamine, isopropanolamine, n-pentanolamine, n-hexanolamine, diethanolamine, N-alkyldiethanolamines, diisopropanolamine, ethylene glycol, propylene glycol, butanediol, pentanediol, hexanediol, 4,4'-bishydroxycyclohexylpropane-(2,2), methoxyethanol, propoxyethanol, butoxyethanol, poly(isobutyl alcohol)s, poly(propyl alcohol)s, poly(ethylene glycol ether)s, poly(propylene glycol ether)s and poly(butylene glycol ether)s. The last-named poly(alkylene glycol ether)s are converted to the corresponding amines during the reaction of the invention by conversion of their free hydroxyl groups.

Both ammonia and primary or secondary aliphatic or cycloaliphatic amines can be used as aminating agents in the hydrogenative amination of alcohols.

When use is made of ammonia as aminating agent the alcoholic hydroxyl groups are first of all converted into free amino groups (—$NH_2$). The primary amines thus formed can react with more alcohol to form the corresponding secondary amines and these in turn react with more alcohol to form the corresponding symmetrical tertiary amines. Depending on the composition of the reaction batch and the reaction conditions used—pressure, temperature, reaction time—preferably primary, secondary, or tertiary amines can be prepared in this way as desired.

Cyclic amines such as pyrrolidines, piperidines, piperazines and morpholines can be prepared in this way from polybasic alcohols by intramolecular hydrogenative amination.

Primary or secondary amines can be used as aminating agents as well as ammonia.

These aminating agents are preferably used for the preparation of unsymmetrically substituted di- or tri-alkylamines, such as ethyldiisopropylamine and ethyldicyclohexylamine. The following mono- and di-alkylamines are preferably used, for example, as aminating agents: methylamine, dimethylamine, ethylamine, diethylamine, propylamine, diisopropylamine, butylamine, pentylamine, hexylamine and cyclohexylamine.

The aminating agent can be used in a stoichiometric amount in relation to the alcoholic hydroxyl group to be aminated. However the process is preferably carried out using an excess of aminating agent, generally more than a fivefold molar excess per mole of alcoholic hydroxyl group to be aminated. Ammonia, in particular, is generally used in a molar excess of from 5 to 250 times, preferably from 10 to 100 times, and more preferably from 25 to 80 times, the molar amount of alcoholic hydroxyl groups which are to be converted. Higher excesses both of ammonia and of primary or secondary amines are possible.

The hydrogen is generally fed to the reaction at a rate of from 5 to 400 L (STP), preferably at a rate of from 50 to 200 L (STP) per mole of alcohol component.

The reaction generally takes place without the use of additional solvent. During the reaction of high molecular weight or highly viscous starting materials or starting compounds or products which are solid at room temperature, it can be advantageous to make supplementary use of a solvent which is inert under the reaction conditions, such as tetrahydrofuran, dioxane, N-methylpyrrolidone, or ethylene glycol dimethyl ether.

Usually the reaction is carried out at temperatures of from 80° to 200° C., preferably from 120° to 230° C. and more preferably from 150° to 220° C. The reaction is generally carried out under a pressure of from 1 to 400 bar. Pressures of from 10 to 250 bar are preferably used however, particularly from 30 to 200 bar.

The use of higher temperatures and a higher overall pressure is possible. The overall pressure in the reaction vessel, which is equal to the sum of the partial pressures of the aminating agent, the alcohol component, and the reaction products formed and of any solvent used at the temperatures stated, is advantageously controlled by forcing in hydrogen to establish the desired reaction pressure.

It can be advantageous as regards the selectivity of the present process to mix the shaped catalyst elements in the reactor with inert packing elements, ie, to "dilute" them as it were. The proportion of the packing elements in such catalyst formulations can be from 20 to 80, preferably from 30 to 60 and more preferably from 40 to 50 percent by volume.

In practice the process is generally carried out by simultaneously feeding the alcohol and the aminating agent to the catalyst, which is usually present in a preferably externally heated fixed bed reactor, at the desired temperature of reaction and the desired pressure. In this process the specific throughput is generally from 0.02 to 3 L, preferably from 0.05 to 2 L and more preferably from 0.1 to 1.6 L of alcohol per liter of catalyst per hour. In this case it is advantageous to heat the reactants, preferably to the temperature of reaction, prior to introduction thereof into the reaction vessel.

The reactor can be operated in both upward and downward modes, ie the reactants can pass both upwardly and downwardly through the reactor. It is obvious that the process can be carried out batchwise or continuously. In both cases the excess aminating agent can be recycled along with the hydrogen. If the conversion achieved during the reaction is incomplete, unconverted starting material can likewise be recycled to the reaction zone.

The excess aminating agent and the hydrogen are removed from the effluent, advantageously after this has been depressurized, and the aminated products obtained are purified by distillation, liquid extraction, or crystallization. The excess aminating agent and the hydrogen are advantageously recycled to the reaction zone. The same applies to any unconverted or incompletely converted alcohol component.

The water of reaction formed in the course of the reaction generally has no adverse effect on the degree of conversion, the reaction rate, the selectivity, or the maximum on-stream time of the catalyst and is therefore advantageously not removed from the reaction product until purification of the latter, by distillation, takes place.

The catalysts of the invention are preferably generally used in the form of solid catalysts. By the term "solid catalyst" is meant a catalyst which, unlike a supported catalyst, consists of catalytically active material only. Solid catalysts can be used by placing the catalytically active material, ground to a powder, in the reaction vessel or by using the catalytically active material, following milling, mixing with molding agents, shaping and tempering, in the form of shaped catalyst elements—for example, as balls, cylinders, rings, or spirals—and placing said elements in the reactor.

The catalytically active material of the catalysts of the invention contains, in addition to oxygen-containing compounds of zirconium, oxygen-containing compounds of nickel, copper and molybdenum.

Since the concentration data relate in each case—unless otherwise stated—to the catalytically active material of the catalyst, the catalytically active material of the catalyst is defined below as the sum of the weights of the catalytically active constituents zirconium, nickel, copper, and molybdenum present in the catalyst, always calculated as $ZrO_2$, $NiO$, $CuO$, or $MoO_3$ respectively, following its last heat treatment and prior to its reduction with hydrogen.

Generally the zirconium oxide content of the catalysts of the invention is between 20 and 85 wt %, preferably from 25 to 60 wt %.

The other components nickel and copper are generally present in a total amount of from 15 to 80 wt %, preferably from 15 to 60 wt %, in particular from 15 to 50 wt %, and molybdenum is generally present in amounts of from 0.1 to 5 wt %, preferably from 0.5 to 3.5 wt %, in the catalytically active material.

Preferred catalysts contain in their catalytically active material from 20 to 85 wt %, preferably from 25 to 60 wt %, of oxygen-containing zirconium compounds, from 1 to 30 wt %, preferably from 10 to 25 wt %, of oxygen-containing copper compounds, from 30 to 70 wt %, preferably from 40 to 70 wt % and more preferably from 45 to 60 wt %, of oxygen-containing compounds of nickel, from 0.1 to 5 wt %, preferably from 0.5 to 3.5 wt %, of oxygen-containing compounds of molybdenum, and from 0 to 10 wt % of oxygen-containing compounds of aluminum and/or manganese.

Various procedures are possible for the preparation of the solid catalysts. They can be obtained, for example, by forming a paste of pulverulent mixtures of the hydroxides, carbonates, oxides, and/or other salts of the components zirconium, nickel, and copper with water followed by extrusion and tempering of the material thus obtained.

Generally however, precipitation methods are used for the preparation of the catalysts of the invention. Thus they can be obtained, for example, by concurrent precipitation of the nickel and copper components from an aqueous salt solution containing these elements by means of mineral bases in the presence of a slurry of a difficultly soluble, oxygen-containing zirconium compound followed by washing, drying and calcination of the precipitate obtained. As difficultly soluble, oxygen-containing zirconium compounds there can be used for example, zirconium dioxide, zirconium oxide hydrate, and zirconium phosphates, borates and silicates. The slurries of the difficultly soluble zirconium compounds can be prepared by suspending fine-grained powders of these compounds in water with vigorous stirring. These slurries are advantageously obtained by precipitating the difficultly soluble zirconium compounds from aqueous zirconium salt solutions by means of mineral bases.

The catalysts of the invention are preferably prepared via concurrent precipitation (mixed precipitation) of all of its components. To this end, an aqueous salt solution containing the catalyst components is advantageously admixed, with heating and stirring, with an aqueous mineral base, in particular an alkali metal base—for example sodium carbonate, sodium hydroxide, potassium carbonate, or potassium hydroxide—until precipitation is complete. The nature of the salts used is not generally crucial. Since, when using this procedure, the water-solubility of the salts is the guiding factor, one criterion to be observed is sufficient water-solubility to allow for the preparation of these relatively highly concentrated salt solutions. It is to be regarded as self-evident that when selecting the salts of the individual components, naturally only those salts are chosen which have anions such as do not lead to false reactions, for example to undesirable precipitations or to the hindrance or prevention of precipitation due to complex formation.

Catalysts of the invention having particularly advantageous properties are obtainable by precipitating a portion of the zirconium component of the catalyst, advantageously from an aqueous zirconium salt solution separately in precipitating equipment by the addition of aqueous mineral bases. Onto the preferably freshly precipitated zirconium oxide hydrate thus obtained the remaining portion of the zirconium component of the catalyst can then be precipitated together with the other catalytically active components, by mixed precipitation as described above. It has been found to be particularly advantageous to effect preliminary precipitation of from 10 to 80 wt %, preferably from 30 to 70 wt % and more preferably from 40 to 60 wt %, of the total amount of zirconium.

The precipitates obtained in these precipitation reactions are generally chemically uniform and consist inter alia of mixtures of the oxides, oxide hydrates, hydroxides, carbonates and insoluble and basic salts of said metals. Ageing of the precipitates may have a favorable effect on their filterability, ie, ageing achieved by leaving them to stand for a while after precipitation, optionally with heating or aeration.

The precipitates obtained in these precipitation reactions are processed in the usual manner to form the catalysts of the invention. After being washed, they are generally dried at from 80° to 200° C. and preferably from 100° to 150° C. and are then calcined. Calcination is generally carried out at temperatures between 300° and 800° C., preferably at from 400° to 600° C. and more preferably at from 450° to 550° C.

Following calcination, the catalyst is advantageously conditioned, for example by milling it to a specific grain size, or by milling it and then mixing it with molding agents such as graphite or stearic acid followed by compression to shaped articles by means of a pelleting press and tempering. The tempering temperatures used in this process are generally the same as those used during calcination.

The catalysts prepared in this manner contain the catalytically active metals in the form of a mixture of their oxygen-containing compounds ie in particular in the form of oxides and mixed oxides.

The catalysts prepared in this manner are stored and, if desired, traded as such. Prior to their use as catalysts for hydrogenative amination they are usually subjected to preliminary reduction. However, they can be used without preliminary reduction if desired, in which case they are then reduced under the conditions of the hydrogenative amination by the hydrogen present in the reactor. To effect preliminary reduction, the catalysts are generally first of all exposed to a nitrogen/hydrogen atmosphere at a temperature of from 150° to 200° C. over a period of from 12 to 20 h, and then treated in a hydrogen atmosphere at from 200° to 300° C. for up to approximately 24 h. In this preliminary reduction process part of the oxygen-containing metal compounds present in the catalysts is reduced to form the corresponding metals, such that these, together with the various oxygen compounds, are present in the active form of the catalyst.

The substituents $R^1$, $R^2$, $R^3$, $R^4$, $R^5$, $R^6$, $R^7$, $R^9$, $R^9$, and $R^{10}$ and indices l, m, and n in the compounds I, II, and III independently have the following meanings:

$R^1$, $R^2$, $R^3$, $R^4$, $R^5$, $R^6$, $R^7$, $R^8$, $R^9$, $R^{10}$ hydrogen, $R^3$, $R^4$ $C_1$–$C_{200}$ alkyl, preferably $C_1$–$C_8$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, n-decyl, 2-n-propyl-n-heptyl, n-tridecyl, 2-n-butyl-n-nonyl and 3-n-butyl-n-nonyl, more preferably isopropyl, 2-ethylhexyl, n-decyl, 2-n-propyl-n-heptyl, n-tridecyl, 2-n-butyl-n-nonyl and 3-n-butyl-n-nonyl and preferably $C_{40}$–$C_{200}$ alkyl such as polybutyl, polyisobutyl, polypropyl, polyisopropyl and polyethyl, more preferably polybutyl and polyisobutyl, $R^1$ and $R^2$ or $R^3$ and $R^4$ or $R^2$ and $R^4$ together form a —(CH$_2$)$_l$—X—(CH$_2$)$_m$ group, $R^1$, $R^2$, $R^3$, and $R^4$ $C_3$–$C_{12}$ cycloalkyl, preferably $C_3$–$C_6$ cycloalkyl such as cyclopropyl, cyclobutyl, cyclopentyl, cyclohexyl, cycloheptyl and cyclooctyl, more preferably cyclopentyl, cyclohexyl and cyclooctyl, aryl, such as phenyl, 1-naphthyl, 2-naphthyl, 1-anthryl, 2-anthryl and 9-anthryl, preferably phenyl, 1-naphthyl and 2-naphthyl, more preferably phenyl, $C_7$–$C_{20}$ alkylaryl, preferably $C_7$–$C_2$ alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, $C_7$–$C_{20}$ aralkyl, preferably $C_7$–$C_2$ phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, more preferably benzyl, 1-phenethyl, and 2-phenethyl, $R^1$, $R^2$ $C_1$–$C_{20}$ alkyl, preferably $C_1$–$C_8$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, more preferably $C_1$–$C_4$ alkyl such as methyl, ethyl, n-propyl, isopropyl, n-butyl, isobutyl, sec-butyl and tert-butyl, $R^3$, $R^4$ $C_1$–$C_{20}$ hydroxyalkyl, preferably $C_1$–$C_8$ hydroxyalkyl, more preferably $C_1$–$C_4$ hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-hydroxymethylethyl, $C_1$–$C_{20}$ alkyl substituted by amino and hydroxy, preferably $C_1$–$C_8$ alkyl substituted by amino and/or hydroxy, more preferably $C_1$–$C_4$alkyl such as N-(hydroxyethyl)aminoethyl and N-(aminoethyl)aminoethyl substituted by amino and/or hydroxy, $C_2$–$C_{30}$ alkoxyalkyl, preferably $C_2$–$C_{20}$ alkoxyalkyl, more preferably $C_2$–$C_8$ alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, more preferably $C_2$–$C_4$ alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl, and 2-methoxyethyl, $R^5$—$(OCR^6R^7CR^8R^9)_n$—$(OCR^6R^7)$, preferably $R^5$—$(OCHR^7CHR^9)_n$—$(OCR^6R^7)$, more preferably $R^5$—$(OCH_2CHR^9)_n$—$(OCR^6R^7)$, $(R^5)_2N$—$(CH_2)_q$, $Y$—$(CH_2)_m$—$NR^5$—$(CH_2)_q$, $R^5$, $R^{10}$ $C_1$–$C_4$ alkyl such as methyl, ethyl, n-propyl, isopropyl, n-butyl, isobutyl, sec-butyl and tert-butyl, preferably methyl and ethyl, more preferably methyl, $R^6$, $R^7$, $R^8$, $R^9$ methyl or ethyl, preferably methyl,

X $CH_2$, oxygen,

N—$R^6$,

Y $N(R^5)_2$, hydroxy, $C_2$–$C_{20}$ alkylaminoalkyl, preferably $C_2$–$C_{16}$ alkylaminoalkyl such as methylaminomethyl, methylaminoethyl, ethylaminomethyl, ethylaminoethyl and isopropylaminoalkyl, $C_3$–$C_{20}$ dialkylaminoethyl, preferably $C_3$–$C_{16}$ dialkylaminoalkyl such as dimethylaminomethyl, dimethylaminoethyl, dialkylaminoethyl, di-n-propylaminoethyl and diisopropylaminoethyl, l an integer from 2 to 4 such as 2, 3 or 4, preferably 2 or 3, more preferably 2, m and q an integer from 1 to 4 such as 1, 2, 3 or 4, preferably 2, 3 or 4, more preferably 2 or 3, $R^5$ $C_{12}$–$C_{40}$ alkylphenyl, preferably $C_{14}$–$C_{40}$alkylphenyl such as 2-, 3-, and 4-nonylphenyl, 2-, 3-, and 4-decylphenyl, 2,3-, 2,4-, 2,5-, 3,4-, and 3,5-dinonylphenyl, 2,8-, 2,4-, 2,5-, 3,4-, and 3,5-didecylphenyl, n an integer from 1 to 10, preferably an integer from 1 to 8 such as 1,2, 3, 4, 5, 6, 7 or 8, more preferably an integer from 1 to 6 such as 1,2, 3, 4, 5 or 6.

The amines that can be produced in the present invention are suitable inter alia as intermediates for the preparation of fuel additives (U.S. Pat. No. 3,275,554; DE-A 2,125,039 and DE-A 3,611,230), surfactants, medicines, plant protectants, and vulcanization promotors.

EXAMPLES

For the evaluation of the mechanical stability of the catalysts a fast screening method was developed. Under the usual conditions of the hydrogenative amination of poly-(isobutene oxo alcohol)s reactions were carried out in batch autoclave tests under standardized conditions over various catalysts. The catalysts described in the present invention were distinguished by their high mechanical stability on completion of the test, particularly when compared with catalysts described in EP-A 1 382,049.

Catalyst preparation

Preparation of catalyst A

An aqueous solution of nickel nitrate, copper nitrate, and zirconium acetate, which contained 4.48% of NiO, 1.52% of CuO, and 2.82% of $ZrO_2$, was precipitated in a stirred vessel at a constant rate of flow simultaneously with a 20% strength aqueous sodium carbonate solution, at a temperature of 70° C., such that the pH measured with a glass electrode was maintained at 7.0.

The suspension obtained was filtered and the filter cake washed with demineralized water until the electrical conductivity of the filtrate was ca 20 µS. Ammonium heptamolybdate was then incorporated into the moist filter cake until the oxide mixture stated below was obtained. Afterwards the filter cake was dried at a temperature of 150° C. in a drying cabinet or a spray dryer. The hydroxide/carbonate mixture obtained in this way was then tempered at a temperature of 500° C. over a period of 4 h.

The catalyst thus obtained had the following composition: 50 wt % of NiO, 17 wt % of CuO, 1.5 wt % of $MoO_3$ and 31.5 wt % of $ZrO_2$. The catalyst powder was mixed with 3 wt % of graphite and compressed to form 6×3 mm pellets. The pellets had a porosity (determined by measuring the water uptake) of 0.20 mL/g and a hardness of 3500 N/cm².

Preparation of catalyst B

For comparative tests a catalyst was prepared in accordance with EP-A 382,049, as follows. A solution of zirconium, copped(II), cobalt(II), and nickel(II) salts was pumped concurrently with a sodium carbonate solution having a density of 1.208 kg/L into precipitating equipment in which freshly precipitated zirconium dioxide was present, suspended in water. The pH of the solution was kept at a constant value of 6.0 during precipitation and raised to pH 7.5 following consumption of the mineral salt solution.

The precipitate was washed, dried to constant weight at 120° C. and calcined to contant weight at 400° C. The crude catalyst material obtained was milled, mixed with 3 wt % of graphite, pelletized, and again calcined at 520° C. for a period of 3 h.

Composition:

76 wt % of Zr, calculated as $ZrO_2$ 4 wt % of Cu, calculated as CuO 10 wt % of Co, calculated as CoO 10 wt % of Ni, calculated as NiO Comparative test carried out using catalyst A and B as described above The reaction was carried out in an autoclave having a capacity of 2 L. The standard stroke stirrer was equipped with a V2A container having a capacity of 100 mL, in which 90 mL of catalyst was placed, in each test. In each test, 450 g of poly(isobutene oxoalcohol) (50% strength solution in dodecane) were caused to react with 450 mL of of liquid ammonia at a hydrogen pressure of 40 bar at 230° C. and a reaction time of 4 h. On completion of the experiment, the finished catalyst was washed 3 times with tetrahydrofuran, dried over a period of 8 h at 125° C. in vacuo (1 mbar), after which the mechanical stability was determined.

The comparative test showed that the mechanical stability on completion of the experiment in the case of usage of catalyst A is distinctly greater than in the case of usage of catalyst B.

TABLE

Comparative tests for mechanical stability

| Catalyst | Type A | Type B |
| --- | --- | --- |
| Lateral hardness prior to test [N] | 110.2 ± 35.2 | 39.9 ± 18.1 |
| Frontal hardness prior to test [N/cm$^2$] | 3909 ± 1084 | 3129 ± 564 |
| Lateral hardness on conclusion of test [N] | 40.0 ± 12.0 | 14.4 ± 8.6 |
| Frontal hardness on conclusion of test [N/cm$^2$] | 1835 ± 334 | 1242 ± 678 |

EXAMPLE 1

Hydrogenative amination of poly(isobutene oxoalcohol)

A continuous high-pressure reactor was packed with 500 cm$^3$ of catalyst A and 1200 cm$^3$ of polyisobutene-oxoalcohol (50% strength solution in dodecane) and 1200 cm$^3$ of liquid ammonia were passed through, per hour. The catalyst temperature was adjusted to 210° C. and the pressure in the reactor was kept constant at 200 bar, by concurrently forcing in hydrogen. Excess ammonia was removed from the effluent by distillation, following depressurization of the latter.

Analysis gave the following values:

Total amine number: 0.54 eq/g of crude effluent

Total acetylation number: 0.58 eq/g of crude effluent

OH number: 0.04 eq 2.2 mg/g of crude effluent

EXAMPLE 2

Hydrogenative amination of tridecanol

A continuous high-pressure reactor was packed with 500 cm$^3$ of catalyst A, and 180 cm$^3$ of tridecanol and 1200 cm$^3$ of liquid ammonia were passed through, per hour. The catalyst temperature was adjusted to 200° C. and the pressure in the reactor was kept constant at 200 bar, by concurrently forcing in hydrogen. Excess ammonia was removed from the effluent, by distillation, following depressurization thereof. The collected effluents were distilled and analyzed by gas chromatography:

73.8% of tridecylamine 25.4% of ditridecylamine

No tridecanol

Remainder 0.7%

EXAMPLE 3

Hydrogenative amination of diisononylphenol×24 butylene oxide

A continuous high-pressure reactor was packed with 500 cm$^3$ of catalyst A, and 100 cm$^3$ of diisononylphenol×24 butylene oxide (Keropur ES 321 3) and 300 cm$^3$ of liquid ammonia were passed through, per hour. The catalyst temperature was adjusted to 220° C. and the pressure in the reactor was kept constant at 200 bar, by concurrently forcing in hydrogen. Excess ammonia was removed from the effluent, by distillation, following depressurization thereof. The analysis of the collected effluents gave the following values:

Total amine number: 0.58 eq/g of crude effluent

Total acetylation number: 0.61 eq/g of crude effluent

OH number: 0.03 eq/g of crude effluent

EXAMPLE 4

Hydrogenative dimethylamination of ethanol

A continuous high-pressure reactor was packed with 500 cm$^3$ of catalyst A, and 1800 cm$^3$ of a mixture of ethanol and dimethylamine in a molar ratio of 4:1 were passed through, per hour. The catalyst temperature was adjusted to 160° C. and the pressure in the reactor was kept constant at 60 bar, by concurrently forcing in hydrogen. Excess ammonia was removed from the effluent, by distillation, following depressurization thereof. The collected effluents were analyzed by gas chromatography:

Dimethylamine: <0.5%

Trimethylamine: 1.5%

Dimethylethylamine: 24.0%

Methyldiethylamine: 1.5%

Ethanol: 60%

Water: 6%

EXAMPLE 5

Hydrogenative amination of diglycol (target, morpholine)

A continuous high-pressure reactor was packed with 500 cm$^3$ of catalyst A, and 90 cm$^3$ of diglycol and 350 cm$^3$ of liquid ammonia were passed through, per hour. The catalyst temperature was adjusted to 200° C. and the pressure in the reactor was kept constant at 200 bar, by concurrently forcing in hydrogen. Excess ammonia was removed from the effluent, by distillation, following depressurization thereof. The collected effluents were analyzed by gas chromatography:

Morpholine: 75.8%

Aminodiglycol: 11.8%

Diglycol: 4.9%

Other by-products: 7.5%

EXAMPLE 6

Hydrogenative amination of diglycol (target, aminodiglycol)

A continuous high-pressure reactor was packed with 500 cm$^3$ of catalyst A, and 270 cm$^3$ of diglycol and 350 cm$^3$ of liquid ammonia were passed through, per hour. The catalyst temperature was adjusted to 200° C. and the pressure in the reactor was kept constant at 200 bar, by concurrently forcing in hydrogen. Excess ammonia was removed from the effluent, by distillation, following depressurization thereof. The collected effluents were analyzed by gas chromatography:

Morpholine: 35.3%
Aminodiglycol: 29.3%
Diglycol: 30.7%
Other by-products: 4.7%

EXAMPLE 7

Hydrogenative amination of ethylglycol

A continuous high-pressure reactor was packed with 500 cm³ of catalyst A, and 150 cm³ of ethyl glycol and 350 cm³ of liquid ammonia were passed through, per hour. The catalyst temperature was adjusted to 210° C. and the pressure in the reactor was kept constant at 200 bar, by concurrently forcing in hydrogen. Excess ammonia was removed from the effluent, by distillation, following depressurization thereof. The collected effluents were analyzed by gas chromatography:

80.7% of ethoxyethylamine
13.9% of di(2-ethoxyethyl)amine
3.6% of ethylglycol
1.8% of other compounds

EXAMPLE 8

Hydrogenative amination of tripropylene glycol

A continuous high-pressure reactor was packed with 500 cm³ of catalyst A, and 250 cm³ of tripropylene glycol and 1500 cm³ of liquid ammonia were passed through, per hour. The catalyst temperature was adjusted to 220° C. and the pressure in the reactor was kept constant at 200 bar, by concurrently forcing in hydrogen. Excess ammonia was removed from the effluent, by distillation, following depressurization thereof. The analysis of the collected effluents gave the following values:

Total amine number: 9.66 eq/g of crude effluent
Total acetylation number: 1.02 eq/g of crude effluent
OH number: 0.52 eq/g of crude effluent
sec-amine number: 0.61 eq/g of crude effluent
tert-amine number: 0.03 eq/g of crude effluent

EXAMPLE 9

Hydrogenative amination of poly(propylene glycol)

A continuous high-pressure reactor was packed with 2200 cm³ of catalyst A, and 50 L of poly(propylene glycol) (average molar mass: 1000) and 240 L of liquid ammonia were passed through, per hour. The catalyst temperature was adjusted to 200° C. and the pressure in the reactor was kept constant at 250 bar, by concurrently forcing in hydrogen. Excess ammonia was removed from the effluent, by distillation, following depressurization thereof. The analysis of the collected effluents gave the following values:

Total amine number: 0.98 eq/g of crude effluent
Total acetylation number: 1.00 eq/g of crude effluent
OH number: 0.02 eq/g of crude effluent
sec/tert-amine number: 0.03 eq/g of crude effluent

EXAMPLE 10

Hydrogenative amination of 2-diisopropylethanolamine

A continuous high-pressure reactor was packed with 500 cm³ of catalyst A, and 180 cm³ of 2-diisopropylethanolamine and 350 cm³ of liquid ammonia were passed through, per hour. The catalyst temperature was adjusted to 200° C. and the pressure in the reactor was kept constant at 200 bar, by concurrently forcing in hydrogen. Excess ammonia was removed from the effluent, by distillation, following depressurization thereof. The collected effluents were analyzed by gas chromatography:

75.7% of N,N-diisopropylethylenediamine
1.0% of N,N-diisopropyl-N'-methylethylenediamine
5.4% of 2-diisopropylethanolamine
17.8% of other compounds

We claim:

1. A process for the preparation of an amine which comprises reacting a primary or secondary alcohol and a nitrogen compound selected from the group consisting of ammonia and primary and secondary amines, at temperatures of from 80° to 250° C. and pressures of from 1 to 400 bar using hydrogen in the presence of a zirconium/copper/nickel catalyst, wherein the catalytically active material contains from 20 to 85 wt % of oxygen-containing zirconium compounds, calculated as $ZrO_2$, from 1 to 30 wt % of oxygen-containing compounds of copper, calculated as CuO, from 30 to 70 wt % of oxygen-containing compounds of nickel, calculated as NiO, from 0.1 to 5 wt % of oxygen-containing compounds of molybdenum, calculated as $MoO_3$ and from 0 to 10 wt % of oxygen-containing compounds of aluminum and/or manganese, calculated as $Al_2O_3$ or $MnO_2$ respectively.

2. A process as claimed in claim 1 for the preparation of an amine of the general formula I

in which $R^1$ and $R^2$ denote hydrogen, $C_1$–$C_{20}$ alkyl, $C_3$–$C_{12}$ cycloalkyl, aryl, $C_7$–$C_{20}$ aralkyl and $C_7$–$C_{20}$ alkylaryl or together form $(CH_2)_l$—X—$(CH_2)_m$, $R^3$ and $R^4$ denote hydrogen, $C_1$–$C_{200}$ alkyl, $C_3$–$C_{12}$ cycloalkyl, $C_1$–$C_{20}$ hydroxyalkyl, $C_1$–$C_{20}$ alkyl substituted by amino and/or hydroxy, $C_2$–$C_{30}$ alkoxyalkyl, $R^5$—$(OCR^6R^7CR^8R^9)_n$—$(OCR^6R^7)$, aryl, $C_7$–$C_{20}$ aralkyl, $C_7$–$C_{20}$ alkylaryl, $(R^5)_2N$—$(CH_2)_q$ and Y—$(CH_2)_m$—$NR^5$—$(CH_2)_q$ or together form $(CH_2)_l$—X—$(CH_2)_m$ or $R^2$ and $R^4$ together form $(CH_2)_l$—X—$(CH_2)_m$, $R^5$ denotes hydrogen, $C_1$–$C_4$ alkyl, or $C_{12}$–$C_{40}$ alkylphenyl, $R^6$, $R^7$, $R^8$, and $R^9$ denote hydrogen, methyl, or ethyl, $R^{10}$ denotes hydrogen or $C_1$–$C_4$ alkyl, X denotes $CH_2$, oxygen, or N—$R^6$, Y denotes $N(R^5)_2$, hydroxy, $C_2$–$C_{20}$ alkylaminoalkyl or $C_3$–$C_{20}$ dialkylaminoalkyl, n is an integer from 1 to 30, l is an integer from 2 to 4, m and q are integers from 1 to 4, from a primary or secondary alcohol of the general formula II $$R^4\text{—}CHR^3\text{—}OH, \quad (II)$$

and a nitrogen compound of the general formula III

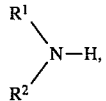
(III)

in which $R^1$, $R^2$, $R^3$ and $R^4$ have the aforementioned meanings, at temperatures of from 80° to 250° C. and pressures of from 1 to 400 bar using hydrogen in the presence of a zirconium/copper/nickel catalyst, wherein the catalytically active material contains from 20 to 85 wt % of oxygen-containing zirconium compounds, calculated as $ZrO_2$, from 1 to 30 wt % of oxygen-containing compounds of copper, calculated as CuO, from 30 to 70 wt % of oxygen-containing compounds of nickel, calculated as NiO, from 0.1 to 5 wt % of oxygen-containing compounds of molybdenum, calculated as $MoO_3$ and from 0 to 10 wt % of oxygen-containing compounds of aluminum and/or manganese, calculated as $Al_2O_3$ or $MnO_2$ respectively.

3. A process for the preparation of an amine from an alcohol and a nitrogen compound using hydrogen in the presence of a zirconium/copper/nickel catalyst as defined in claim 1, wherein the catalytically active material contains from 40 to 70 wt % of oxygen-containing compounds of nickel, calculated as NiO.

4. A process for the preparation of an amine from an alcohol and a nitrogen compound using hydrogen in the presence of a zirconium/copper/nickel catalyst as defined in claim 1, wherein the catalytically active material contains from 45 to 60 wt % of oxygen-containing compound of nickel, calculated as NiO.

5. A process for the preparation of an amine from an alcohol and a nitrogen compound using hydrogen in the presence of a zirconium/copper/nickel catalyst as defined in claim 1, wherein the catalytically active material contains from 0.5 to 3.5 wt % of oxygen-containing compound of molybdenum, calculated as $MoO_3$.

6. A process for the preparation of an amine from an alcohol and a nitrogen compound using hydrogen in the presence of a zirconium/copper/nickel catalyst as defined in claim 1, wherein the catalytically active material contains from 25 to 60 wt % of oxygen-containing zirconium compound, calculated as $ZrO_2$.

7. A process for the preparation of an amine from an alcohol and a nitrogen compound using hydrogen in the presence of a zirconium/copper/nickel catalyst as defined in claim 1, wherein the catalytically active material contains from 10 to 25 wt % of oxygen-containing compound of copper, calculated as CuO.

8. A process for the preparation of an amine from an alcohol and a nitrogen compound using hydrogen in the presence of a zirconium/copper/nickel catalyst as defined in claim 1, wherein the reaction is carried out at temperatures of from 120° to 230° C.

9. A process for the preparation of an amine from an alcohol and a nitrogen compound using hydrogen in the presence of a zirconium/copper/nickel catalyst as defined in claim 1, wherein the reaction is carried out under pressures of from 10 to 250 bar.

10. A process for the preparation of an amine from an alcohol and a nitrogen compound using hydrogen in the presence of a zirconium/copper/nickel catalyst as defined in claim 1, wherein the reaction is carried out under pressures of from 30 to 220 bar.

* * * * *